(12) United States Patent
Herb et al.

(10) Patent No.: US 6,179,586 B1
(45) Date of Patent: Jan. 30, 2001

(54) DUAL DIAPHRAGM, SINGLE CHAMBER MESOPUMP

(75) Inventors: William R. Herb; J. David Zook, both of Minneapolis; Cleopatra Cabuz, Edina, all of MN (US)

(73) Assignee: Honeywell International Inc., Morristown, NJ (US)

(*) Notice: Under 35 U.S.C. 154(b), the term of this patent shall be extended for 0 days.

(21) Appl. No.: 09/408,651

(22) Filed: Sep. 15, 1999

(51) Int. Cl.$^7$ ................................................. F04B 43/00
(52) U.S. Cl. ........................ 417/480; 417/322; 417/413.1
(58) Field of Search ............................... 137/512.4, 501; 251/65; 417/413.1, 413.3, 413.2, 32.2, 480; 604/131

(56) References Cited

U.S. PATENT DOCUMENTS

| | | | |
|---|---|---|---|
| 4,646,781 | * 3/1987 | Richter | 417/413.1 |
| 5,082,242 | 1/1992 | Bonne et al. | 251/129.01 |
| 5,176,358 | 1/1993 | Bonne et al. | 251/30.05 |
| 5,180,623 | 1/1993 | Ohnstein | 428/209 |
| 5,244,537 | 9/1993 | Ohnstein | 156/643 |
| 5,322,258 | * 6/1994 | Bosch et al. | 251/65 |
| 5,323,999 | 6/1994 | Bonne et al. | 251/11 |
| 5,336,062 | * 8/1994 | Richter | 417/413.2 |
| 5,368,571 | * 11/1994 | Horres, Jr. | 604/131 |
| 5,441,597 | 8/1995 | Bonne et al. | 216/2 |
| 5,529,465 | * 6/1996 | Zengerle et al. | 417/413.2 |
| 5,536,963 | * 7/1996 | Polla | 257/417 |
| 5,725,363 | * 3/1998 | Bustgens et al. | 417/413.3 |
| 5,836,750 | 11/1998 | Cabuz | 417/322 |
| 5,839,467 | * 11/1998 | Saaski et al. | 137/501 |
| 6,106,245 | * 8/2000 | Cabuz | 417/322 |
| 6,109,889 | * 8/2000 | Zengerle et al. | 417/413.2 |
| 6,116,863 | * 9/2000 | Ahn et al. | 417/322 |

OTHER PUBLICATIONS

Wagner et al Journall IEEE Jun. 1996.

\* cited by examiner

Primary Examiner—Teresa Walberg
Assistant Examiner—Leonid Fastovsky
(74) Attorney, Agent, or Firm—John G. Shudy, Jr.

(57) ABSTRACT

A diaphragm pump, which is preferably electrostatically actuated, but which may be activated by other forces such as electromagnetic or piezoelectric actuation. The pump is formed by a pump body having a pump chamber formed therein. First and second diaphragms each having a set of valve holes in the diaphragm surface thereof are mounted in the chamber. Also provided are at least one inlet and at least one outlet port for communication with the pump chamber. The ports are positioned for sealing contact with the diaphragms at points that are not aligned with the holes in the diaphragms. A driver electrostatically actuates the diaphragms to cause diaphragm movement to a plurality of diaphragm positions to control flow of fluid through the pump. The first position is when the diaphragms are spaced from one another and from the ports to permit flow of fluid through the pump chamber. The second position is when the diaphragms are in diaphragm surface contact with the sets of holes mutually nonaligned to form a seal between the diaphragms. The third position is when a diaphragm is in diaphragm surface contact with the ports to form the sealing contact.

36 Claims, 2 Drawing Sheets

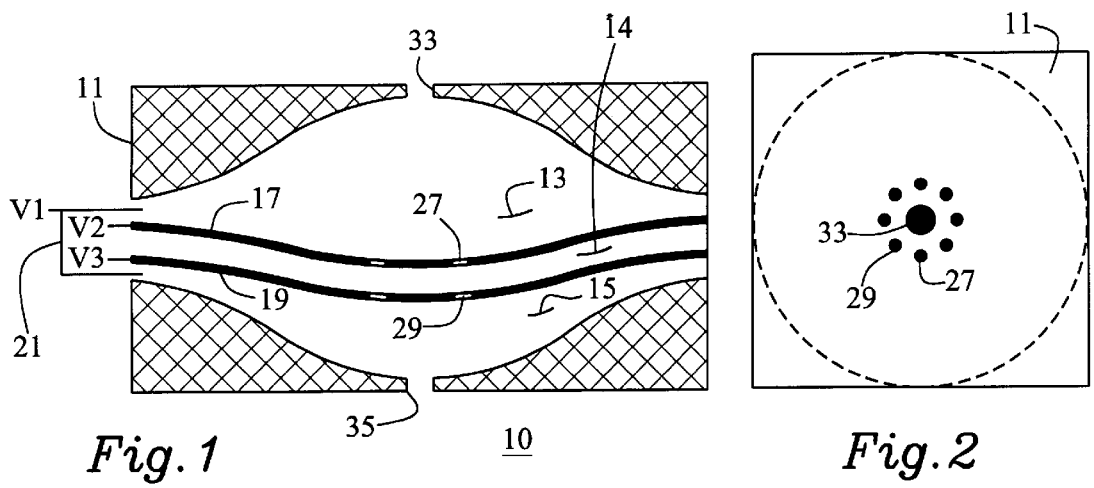
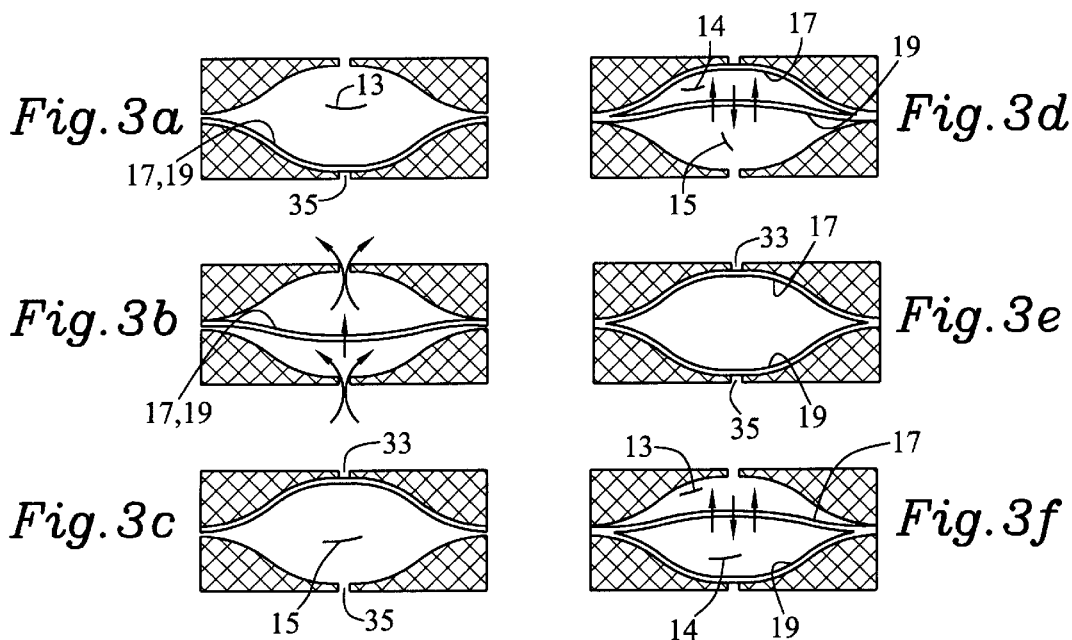
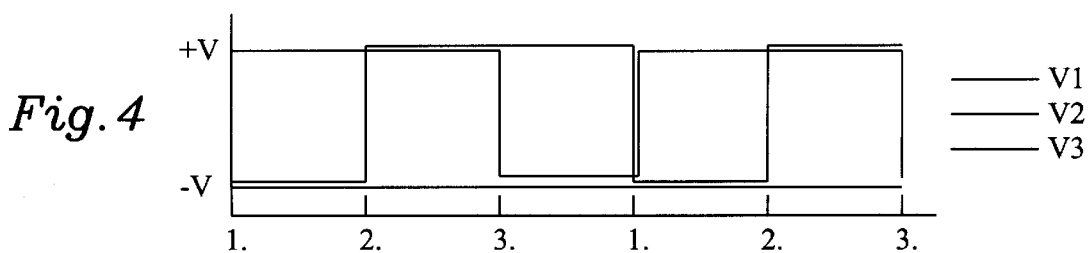

DUAL DIAPHRAGM, SINGLE CHAMBER MESOPUMP

FIELD OF THE INVENTION

The present invention relates to a mesopump. More particularly the invention relates to a mesopump having reduced pump volume and weight for a given fluid pumping rate due to its compact design. The Government may have rights in this invention pursuant to Contract No. DABT63-97-C-0071, awarded by the Department of the Army.

BACKGROUND OF THE INVENTION

Modern industrial, commercial, aerospace and military systems depend critically on reliable pumps for fluid handling. The trends in fluid handling systems are toward smaller, more distributed and more portable systems for increasing uses in instrumentation and control.

Although important advances in pump technology have been made in the past few decades, progress has reached saturation in terms of ability to reduce pump size, weight and power requirements. There is a significant gap between the technology for conventional pumps, including the so-called ìmicropumps, ì and pumps that are based on microelectronics technology.

The pumping capability of these micropumps is in one to tens of microliters per minute range. This makes them useful for applications such as implantable systems for drug delivery or micro dosage in chemical analysis systems but such pumping speeds are many orders of magnitude smaller than those required in sampling applications.

A number of United States patents have been granted on apparatus and devices generally relating to microvalve construction and control. For example, U.S. Pat. No. 5,082,242 to Bonne et al describes a microvalve that is an integral structure made on one piece of silicon such that the device is a flow through valve with inlet and outlet on opposite sides of the silicon wafer. The valves are closed by contact with a valve seat where surfaces must be matched in order to avoid degradation of valve performance. Two patents, U.S. Pat. Nos. 5,180,623 and 5,244,527 are divisional patents relating to the first mentioned patent.

Another family of patents describe fluid control employing microminiature valves, sensors and other components using a main passage between one inlet and exit port and additionally a servo passage between inlet and outlet ports. The servo passage is controlled by a control flow tube such that tabs are moved electrostatically. U.S. Pat. No. 5,176,358 to Bonne et al teaches such a fluid regulating device, while divisional U.S. Pat. Nos. 5,323,999 and 5,441,597 relate to alternative embodiments.

An additional concept is disclosed by Wagner et al in the June, 1996, edition of the IEEE Journal, pages 384–388, in which two buckled $Si/SiO_2$ membranes spanning air filled cavities having enclosed driving electrodes. A coupled membrane system is disclosed in which a first silicon membrane is switched by electrostatic force which, in turn, presses air through a channel to push the second silicon membrane up.

In both of these patented systems and in the concept described by Wagner et al, silicon semiconductor chips are employed. Silicon technology is, in fact, a host for a number of microsensors. The possibility of fabricating fully integrated systems led to the development of some of the above described valves and the like. However, the displacements available at the microscale and the materials available in silicon technology are not the best for such applications. The achievable pumping rates are very small ($\mu l$ to ml/min) at the best. Additionally the structures tend to become complicated and expensive. Of major concern also is the fact that silicon is not compatible with many biological materials, thus eliminating virtually an entire field of end use.

Current sampling pumps for vapor and particle detection are much larger than the instruments they support. In order to be effective for many missions, the sampling rate should be comparable to human breathing, i.e., 10 liters per minute (lpm) or more. The pumps must supply this flow against pressure drops of one psi or more, corresponding to pneumatic output loads exceeding a watt and input power requirements exceeding ten watts. Current system using rotating motors are power hungry, noisy and have limited lifetimes. Mesoscopic pumps with no rotating or sliding parts and high electrical-to-pneumatic conversion efficiencies would be able to dramatically increase the capabilities and effectiveness of military systems that detect chemical, biological, explosive and other agents.

Several versions of these mesopumps are disclosed in U.S. Pat. No. 5,836,750, by Cleopatra Cabuz, entitled Electrostatically Actuated Mesopump Having a Plurality of Elementary Cells. The mesopumps described therein and other more primitive pumps all use a plurality of chambers, such as, for example, three or four chambers, each of which having one diaphragm. While admirably suited for their intended use, some applications may, in the future, be limited by the size and compactness of these prior art mesopumps. Also, in some applications for these mesopumps, the presence of lateral channels and the resulting dead space again limit their applicability. Present day prior art mesopumps also require molding of extra ports to provide pressure relief for unused diaphragm surfaces.

It would be of great advantage in the art if a more compact, lighter weight mesopump could be provided for any given fluid pumping rate.

It would be another great advance in the art if mesopumps could be developed with inlet and outlet ports in the center of the chamber to eliminate lateral channels.

Yet another advance would be achieved if mesopumps could be developed which have no need for molding extra ports for pressure relief.

Other advantages will appear hereinafter.

SUMMARY OF THE INVENTION

It has now been discovered that the above and other objects of the present invention may be accomplished in the following manner. Specifically, the present invention provides an electrostatically actuated diaphragm pump. The pump consists of a single molded plastic chamber with two thin diaphragms staked directly on top of each other. The diaphragms may be actuated with electrostatic, electromagnetic, or piezoelectric methods. The electrostatic actuation approach may be implemented in a similar manner to previous designs such as those in the above-referenced patent applications and patents.

The unique feature of the present invention is the use of a single chamber for pumping, as distinguished from the prior art where three chambers are required. Each diaphragm has its own set of valving holes, wherein the holes in the upper and lower diaphragm are offset so that the surfaces form a sealed surface when they are electrostatically pulled together, yet allow flow through the diaphragm when separated.

At least one inlet port and at least one outlet port are provided in the pump body for communication with the pump chamber. The ports are positioned to be sealed by the diaphragm by insuring contact with the diaphragms at a point nonaligned with the holes in the diaphragm.

The inlet port may be located on the top of the pump chamber for engagement with the first diaphragm to open and close the inlet port. Likewise, the outlet port may be positioned on the bottom of the pump chamber for engagement with the second diaphragm to open and close the outlet port. Since the pump of this invention is reversible, of course, the bottom and top are mere nomenclature and reverse terminology could be used to refer to the inlet/outlet positions.

When the diaphragms are spaced from one another, flow of fluid takes place through the pump chamber. When the diaphragms are in mutual in diaphragm surface contact, a seal is formed to keep the fluid on which ever side of the diaphragms it is at that time. When a diaphragm is in diaphragm surface contact with inlet or outlet port, it seals the port to prevent fluid flow into or out of the pump.

The pumps of the present invention may be formed into an array formed from a plurality of electrostatically actuated diaphragm pumps according to the present invention. These plurality of pumps may be connected through the inlet and outlet ports in parallel to form a sheet-like array, and, even to form multiple layers of sheets of the pumps. Alternatively, the plurality of pumps may be connected through the inlet and outlet ports in series. Both forms are contemplated by the present invention.

BRIEF DESCRIPTION OF THE DRAWINGS

For a more complete understanding of the invention, reference is hereby made to the drawings, in which:

FIG. 1 is an enlarged, cross section view of a pump according to this invention;

FIG. 2 is a top or plan view of the device of FIG. 1;

FIGS. 3a–3f are schematic illustration of the operation of the pump shown in FIG. 1;

FIG. 4 is a schematic diagram illustrating one sequence of control voltages for operation of the pump shown in FIG. 1;

DETAILED DESCRIPTION OF THE PREFERRED EMBODIMENT

Figure 5:
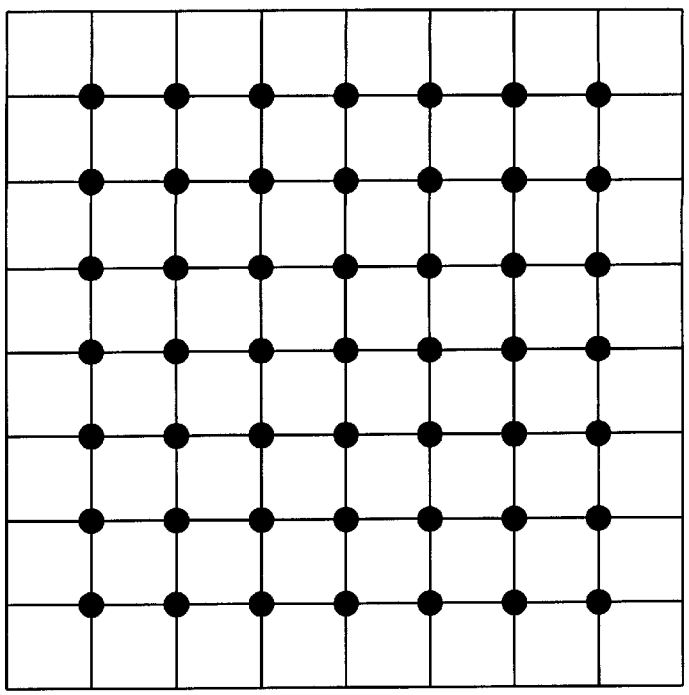
FIG. 5 is a schematic illustration of a four layer parallel array of pump cells of the type shown in FIG. 1.

Turning now to the drawings, FIG. 1 shows the present invention, 10 generally, in cross section, with a body 11 defining a chamber having an upper region 13 a middle region 14 and a lower region 15. The chamber is separated into three regions by the upper and lower diaphragms 17 and 19, respectively, and the volume of each region is determined by the position of the diaphragms. Control electronics 21 provides voltage potentials V1, V2 and V3.

In one embodiment, the upper and lower surfaces of each diaphragm has a separate electrode, as do the upper and lower surfaces of the chamber. In another embodiment, the upper and lower surfaces of each diaphragm and the upper and lower surfaces of the bump chamber may be shorted to the same potential, so that only three control voltages are required. It is known to move diaphragms in chambers electrostatically by application of a voltage to one or more electrodes, and it is contemplated that the present invention will employ those techniques to accomplish the movements of diaphragm into and out of contact with each other and with the chamber itself. Each electrode consists of a conductive metal layer coated with a dielectric to prevent shorting between electrodes, as is known in the art.

Diaphragms 17 and 19 have a plurality of holes 27 and 29, respectively, which permit passage of fluid through the diaphragm. Holes 27 and 29 are nonaligned or positioned so that no hole in diaphragm 17 overlays any hole in diaphragm 19. FIG. 2 illustrates this arrangement, with the upper holes 27 in solid on diaphragm 17, and lower holes 29 in dotted line to illustrate they are located on lower diaphragm 29. When the two diaphragms 17 and 19 are electrostatically pulled together, they form a sealed surface, yet allow flow through the diaphragm if actuated individually. To complete the description of the pump shown in FIG. 1, upper port 33 communicates with upper chamber 13 and lower port 35 communicates with lower chamber 15. The upper chamber region 13 communicates with the middle region 14 via the upper holes 27, and the lower chamber region 15 communicates with the middle region 14 via the lower holes 29. Since fluid flow can be either in or out of port 33 and 35, both ports 33 and 35 will serve as an inlet or an outlet, depending on the configuration of the pump and attendant equipment during use of the pump.

FIGS. 3a–3f illustrate a pumping sequence where the inlet is on the bottom. An opposite configuration is equally appropriate since the pump is completely reversible. FIG. 3a illustrates the orientation where both diaphragms 17 and 19 have been pulled down, thus sealing lower port 35. Fluid is assumed to be contained in upper chamber 13, while middle chamber 14 and the lower chamber 15 are essentially eliminated by the position of the two diaphragms 17 and 19. As noted above, holes 27 and 29 in diaphragms 17 and 19 do not align with each other or with either port 33 or 35, to effect the desired seal. FIG. 3b illustrates the initiation of the pump stroke by simultaneously moving diaphragms 17 and 19 together upward toward the top. FIG. 3c shows completion of the pump stroke, with both diaphragms 17 and 19 pushed up, thus sealing upper port 33. All of the fluid in chamber 13 of FIG. 3a has been expelled in FIG. 3c through upper port 33 and lower port 35 is open, so that the fluid is drawn into the lower chamber 15 through lower port 35. In FIG. 3d, the upper diaphragm 17 remains in sealing relationship with upper port 33 while lower diaphragm 19 is pulled down, causing the fluid in lower chamber 15 to transfer to middle chamber 14 via holes 29. FIG. 3e illustrates the orientation of the lower diaphragm 19 completely pulled down to seal the lower port 35 while upper diaphragm 17 remains sealing upper port 33. Finally, FIG. 3f illustrates the midpoint of movement of upper diaphragm 17 down toward lower diaphragm 19, wherein fluid may be pulled from the middle chamber 14 into the upper chamber 13 to result in the orientation shown initially in FIG. 3a.

FIG. 4 illustrates schematically a possible sequence of control voltages for the pump operation described above, where V1 remains at a +V value, V2 remains at a −V value, and V3 alternates between +V and −V as illustrated, causing the electrostatic activation of diaphragms 17 and 19 as described with respect to FIGS. 3a–3f.

As noted above, the dual diaphragm pump design of the present invention differs from prior art designs in that each pump channel has only one chamber, nominally divided into an upper region 13, middle region 14 and lower region 15, depending on the location of the diaphragms 17 and 19. The three stages of prior art pumping action is, in effect, contained in the single chamber of block 11.

The design of the present invention is much more compact, with only one molded chamber for each pumping channel. Thus the total pump volume and weight required for a given fluid pumping rate is smaller than prior art designs. The inlet and outlet ports are both in the center of the chamber, eliminating the use of lateral channels. This will permit an increase of pumping rate because of the elimination of lateral channels. Clearly, FIG. 1 and others show how dead space has been eliminated, particularly since lateral channels are absent. Additionally, since both sides of the diaphragms are used in the pumping process, there is no need to mold in extra ports to provide pressure relief for unused diaphragm surfaces. Finally, the pump is reversible.

Figure 6A:
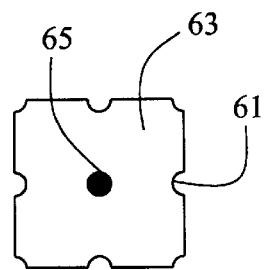
FIGS. 6a and 6b illustrate two alternative shapes for pump bodies for pumps similar to the pump shown in FIG. 1.
Figure 6B:
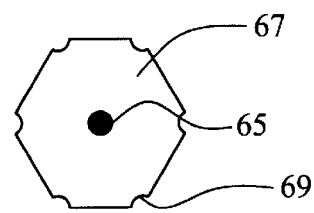
Figure 7:
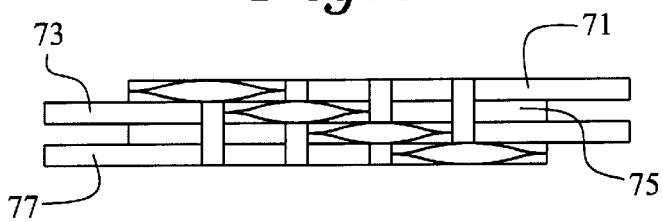
FIG. 7 is a schematic cross section illustration of a four layer pump array.
Figure 8:
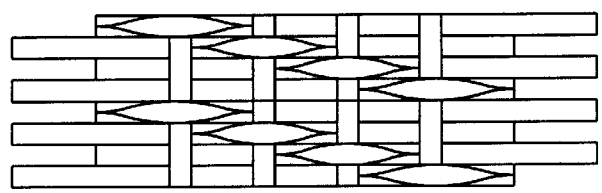
FIG. 8 is a schematic cross section illustration of two four layer pump arrays of FIG. 7, stacked in series.

While stacking parallel array sheets of the dual diaphragm pumps of this invention normally would put the pumps in series, FIGS. 5, 7 and 8 illustrates a pump stacking arrangement in which up to four layers of pumps operate in parallel. As shown in FIG. 6a, flow through channels 61 may be placed in individual bodies 63, with inlet/outlet 65 in the center of body 63, or pump body 67 can be hexagonal in shape, for example, with a central inlet/outlet 65 and flow through channels 69 at each corner of hexagon body 67. In FIG. 7 each layer is offset appropriately. This doubles the linear density of inlet/outlet ports over a single layer of pumps. FIG. 7 shows four layers 71, 73, 75, and 77. FIG. 8 illustrates a pair of four layer pump arrays stacked in series.

Figure 9:
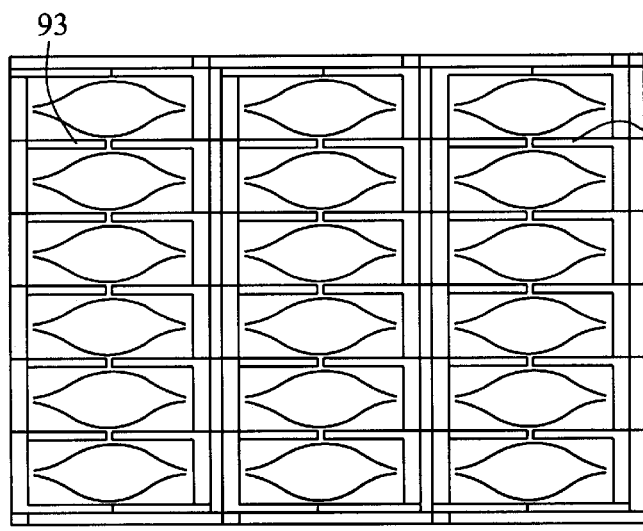
FIG. 9 is a schematic cross section illustration of a second configuration for massively parallel arrays of the pump of FIG. 1.

FIG. 9 illustrates a second configuration for massively parallel arrays of the type shown in FIG. 1. Use of lateral channels 93 for inlet porting and lateral channels 95 for outlet porting permits the number of pump layers stacked on top of each other to be much greater, so a cube shaped array could be formed.

While particular embodiments of the present invention have been illustrated and described, it is not intended to limit the invention, except as defined by the following claims.

What is claimed is:

1. A diaphragm pump, comprising:
   a pump body having a pump chamber formed therein;
   a first diaphragm having a first set of valve holes in the diaphragm surface thereof and a second diaphragm having a second set of valve holes in the diaphragm surface thereof;
   at least one inlet port and at least one outlet port in said pump body for communication with said pump chamber, said at least one inlet and outlet ports being positioned for sealing contact with one of said first and second diaphragms at a point nonaligned with said holes in said diaphragm; and
   a driver for actuating said first and second diaphragms to cause diaphragm movement to a plurality of diaphragm positions to control flow of fluid through said pump;
   a first of said diaphragm positions being said first and second diaphragms spaced from one another and from at least one inlet and outlet ports to permit flow of fluid through said pump chamber;
   a second of said diaphragm positions being said first diaphragm and said second diaphragm in diaphragm surface contact, said first and second set of holes being mutually nonaligned to permit said diaphragm surfaces to form a seal when in said diaphragm surface contact; and
   a third of said diaphragm positions being at least one of said first and second diaphragm in diaphragm surface contact with said at least one inlet and outlet ports to form said sealing contact.

2. The pump of claim 1, which includes an inlet port on said pump chamber for engagement with said first diaphragm to open and close said inlet port.

3. The pump of claim 1, which includes an outlet port on said pump chamber for engagement with said second diaphragm to open and close said outlet port.

4. The pump of claim 1, which includes an inlet port on said pump chamber for engagement with said first diaphragm to open and close said inlet port, and an outlet port on said pump chamber for engagement with said second diaphragm to open and close said outlet port.

5. An array formed from a plurality of diaphragm pumps according to claim 1.

6. The array of claim 5, wherein said plurality of diaphragm pumps are connected through said inlet and outlet ports in parallel to form a sheet-like array.

7. The array of claim 6, wherein said plurality of diaphragm pumps are electrostatically actuated.

8. The array of claim 6, wherein said plurality of diaphragm pumps are connected through said inlet and outlet ports in parallel to form multiple layers of sheets of said pumps.

9. The array of claim 5, wherein said plurality of diaphragm pumps are connected through said inlet and outlet ports in series.

10. The array of claim 9, wherein said plurality of diaphragm pumps are electrostatically actuated.

11. A diaphragm pump, comprising:
    pump body means for defining a pump chamber;
    first diaphragm means for movement in said pump chamber, said first diaphragm means having a first set of valve holes in the diaphragm surface thereof:
    second diaphragm means for movement in said pump chamber, said second diaphragm means having a second set of valve holes in the diaphragm surface thereof;
    inlet port means and outlet port means in said pump body means for communication with said pump chamber, said inlet and outlet port means being positioned for sealing contact with one of said first and second diaphragm means at a point nonaligned with said holes in said diaphragm; and
    driver means for actuating said first and second diaphragm means to cause diaphragm movement to a plurality of diaphragm positions to control flow of fluid;
    a first of said diaphragm positions being said first and second diaphragm means spaced from one another and from inlet and outlet port means to permit flow of fluid through said pump chamber;
    a second of said diaphragm positions being said first diaphragm and second diaphragm means in diaphragm surface contact, said first and second set of holes being mutually nonaligned to permit said diaphragm surfaces to form a seal when in said diaphragm surface contact; and
    a third of said diaphragm positions being at least one of said first and second diaphragm means in diaphragm surface contact with said inlet and outlet port means to form said sealing contact.

12. The pump of claim 11, wherein said inlet port means is positioned on said pump chamber for engagement with said first diaphragm means to open and close said inlet port means.

13. The pump of claim 11, wherein said outlet port means is positioned on said pump chamber for engagement with said second diaphragm means to open and close said outlet port means.

14. The pump of claim 11, wherein said inlet port means is positioned on said pump chamber for engagement with said first diaphragm means to open and close said inlet port means, wherein said outlet port means is positioned on said pump chamber for engagement with said second diaphragm means to open and close said outlet port means.

15. An array formed from a plurality of diaphragm pumps according to of claim 11.

16. The array of claim 15, wherein said plurality of diaphragm pumps are connected through said inlet and outlet ports in parallel to form a sheet-like array.

17. The array of claim 16, wherein said plurality of diaphragm pumps are connected through said inlet and outlet ports in parallel to form multiple layers of sheets of said pumps.

18. The array of claim 17, wherein said plurality of diaphragm pumps are electrostatically actuated.

19. The array of claim 15, wherein said plurality of diaphragm pumps are connected through said inlet and outlet ports in series.

20. The array of claim 19, wherein said plurality of diaphragm pumps are electrostatically actuated.

21. A method of pumping fluids using a diaphragm pump, comprising the steps of:

introducing fluid into a pump body having a pump chamber formed therein through at least one inlet in communication with said pump chamber, said fluid being drawn into said pump chamber by actuating a first diaphragm having a first set of valve holes in the diaphragm surface thereof away from said inlet;

actuating a second diaphragm having a second set of valve holes in the diaphragm surface thereof to a position to permit said fluid to flow through said second diaphragm surface when said first and second diaphragms are not in diaphragm surface contact; and withdrawing fluid from said pump chamber through at least one outlet port in said pump body in communication with said pump chamber, said fluid being withdrawn from said pump chamber by moving said first and said second diaphragms separately to diaphragm surface contact proximate said inlet to thereby make sealing contact to prevent fluid from flowing through said diaphragm holes, and thereafter moving said first and second diaphragms together while maintaining said sealing contact to expel said fluid through said outlet port.

22. The method of claim 21, wherein said inlet port is on said pump chamber for engagement with said first diaphragm.

23. The method of claim 21, wherein said outlet port is on said pump chamber for engagement with said second diaphragm.

24. The method of claim 21, wherein said inlet port is on said pump chamber for engagement with said first diaphragm, and wherein said outlet port is on said pump chamber for engagement with said second diaphragm.

25. The method of claim 21 wherein a plurality of diaphragm pumps are aligned in an array.

26. The array of claim 25, wherein said plurality of diaphragm pumps are connected through said inlet and outlet ports in parallel to form a sheet-like array.

27. The array of claim 26, wherein said plurality of diaphragm pumps are electrostatically actuated.

28. The array of claim 25, wherein said plurality of diaphragm pumps are connected through said inlet and outlet ports in parallel to form multiple layers of sheets of said pumps.

29. The array of claim 28, wherein said plurality of diaphragm pumps are electrostatically actuated.

30. The array of claim 25, wherein said plurality of diaphragm pumps are connected through said inlet and outlet ports in series.

31. The array of claim 30, wherein said plurality of diaphragm pumps are electrostatically actuated.

32. A diaphragm pump, comprising:

a pump body having a pump chamber formed therein;

at least two diaphragms having holes in the surface thereof;

an inlet port and an outlet port in said pump body for communication with said pump chamber, said inlet and outlet ports each being positioned for sealing contact with one of said diaphragms at a point nonaligned with said holes in said diaphragm; and a driver for actuating said diaphragms to control flow of fluid through said pump.

33. An array formed from a plurality of diaphragm pumps according to of claim 32 which are connected through said inlet and outlet ports in parallel to form a sheet-like array.

34. The array of claim 33, wherein said plurality of diaphragm pumps are electrostatically actuated.

35. An array formed from a plurality of diaphragm pumps according to of claim 32 which are connected through said inlet and outlet ports in series to form a sheet-like array.

36. The array of claim 35, wherein said plurality of diaphragm pumps are electrostatically actuated.

* * * * *